(12) United States Patent
Onoda et al.

(10) Patent No.: US 6,735,464 B2
(45) Date of Patent: May 11, 2004

(54) ELECTROCARDIOGRAPH SYSTEM AND ITS COMMUNICATION DEVICE

(75) Inventors: Masahiro Onoda, Kanagawa (JP); Kouichi Inoue, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 161 days.

(21) Appl. No.: 10/012,300

(22) Filed: Dec. 12, 2001

(65) Prior Publication Data

US 2002/0091331 A1 Jul. 11, 2002

(30) Foreign Application Priority Data

Dec. 13, 2000 (JP) ........................................ 2000-379251

(51) Int. Cl.[7] .............................................. A61B 5/0402
(52) U.S. Cl. ....................................................... 600/509
(58) Field of Search ................................. 600/509–525

(56) References Cited

U.S. PATENT DOCUMENTS

| | | |
|---|---|---|
| 4,830,021 A | 5/1989 | Thornton |
| 5,092,340 A | 3/1992 | Yamaguchi et al. |
| 5,284,151 A | 2/1994 | Omoda |
| 5,862,803 A | 1/1999 | Besson et al. |
| 6,049,730 A | 4/2000 | Kristbjarnarson |

FOREIGN PATENT DOCUMENTS

| | | |
|---|---|---|
| EP | 0 299 667 A1 | 1/1989 |
| JP | 62-66845 A | 3/1987 |
| JP | 3-47094 B2 | 7/1991 |
| JP | 5-7560 A | 1/1993 |
| JP | 5-42117 A | 2/1993 |
| JP | 9-56684 A | 3/1997 |
| JP | 9-56686 A | 3/1997 |
| JP | 9-56687 A | 3/1997 |
| JP | 9-56687 A1 | 3/1997 |
| WO | WO 98/43537 A1 | 10/1998 |

*Primary Examiner*—Scott M. Getzow
(74) *Attorney, Agent, or Firm*—Burns, Doane, Swecker & Mathis, LLP

(57) ABSTRACT

An electrocardiograph system has an electrocardiograph transmitting cardiograms produced to outside equipment, and a communication device wirelessly communicating with the electrocardiograph. The communication device accepts a subject's posture selected from multiple posture options, and transmits a specific instruction signal to the electrocardiograph upon receiving the selection. The electrocardiograph stores a cardiogram produced when the instruction signal is received from the communication device as a reference cardiogram corresponding to the selected posture discriminating it from other cardiograms.

20 Claims, 8 Drawing Sheets

ID:ES COMMUNICATION DEVICE

ELECTROCARDIOGRAPH SYSTEM AND ITS COMMUNICATION DEVICE

BACKGROUND OF THE INVENTION

1. Field of the Invention

The present invention relates to an electrocardiograph system and a communication device for it.

2. Description of the Related Art

It is generally known that different cardiograms can be obtained depending on the postures of the subject (the person being diagnosed). Even if the subject is healthy, changes may occur on cardiograms simply due to a change in the postures of the subject. In order to eliminate the effects of posture changes so that proper diagnosis can be made, the device user such as a medical operator must prepare in advance by recording typical cardiograms of the subject at various postures on recording paper as the reference cardiograms. In analyzing the cardiogram obtained for a predetermined time period, the user must compare the cardiograms of the subject with the reference cardiograms. As a result, the user will be able to judge if a change on a cardiogram is due to a posture or illness of the subject.

Cardiograph systems are proposed in recent years wherein reference cardiograms are recorded in the memory devices built into the electrocardiographs instead of recording on paper so that the cardiograms collected in actual diagnoses can be compared with the reference cardiograms by computers.

For example, the Japanese Patent Application No. 9-56687 filed on Aug. 22, 1995 disclosed a cardiogram measuring system. The cardiogram measuring system is equipped with a portable electrocardiograph capable of storing obtained cardiograms and an analyzing device that receives the cardiograms from the electrocardiograph and analyzes them.

The portable electrocardiograph has a capability of measuring and storing reference cardiograms in advance of measuring cardiograms to be analyzed. The portable electrocardiograph itself is equipped with multiple switches. Specifically, it is equipped with switches corresponding to the side lying, standing, walking and running conditions. For example, in order to produce a reference cardiogram for the side lying condition, the subject lies on the side of his/her body while turning on the switch for the lying condition. A cardiogram for the side lying condition is then produced and stored in the memory, after which follows a process of measuring for the predetermined time period a cardiogram to be analyzed.

However, the above-mentioned cardiogram measuring system has the following problems. Since the portable electrocardiograph for measuring and storing cardiograms is equipped with components such as switches for selecting the conditions of the subject, it is difficult to reduce the size of the portable electrocardiograph that is to be attached to the subject. Moreover, it is difficult to make it waterproof because of the components such as switches.

Moreover, while the patent publication disclosed the idea of storing the reference cardiograms corresponding to simpler conditions of the subject, it failed to disclose the idea of storing reference cardiograms corresponding to more specifically classified postures. Consequently, it is impossible to store reference cardiograms corresponding to more specifically classified postures including a standing, a face-up lying, a right side lying, and a left side lying. For the purpose herein, the standing position denotes the position wherein the subject is standing, the face-up lying position denotes the position wherein the subject is lying on his/her back, the right side lying position denotes the position wherein the subject is lying on his/her right side of the body, and the left side lying position denotes the position wherein the subject is lying on his/her left side of the body.

Further, it is difficult for the cardiogram measuring system to display for confirmation the waveforms of reference cardiograms as static images corresponding to the standing, face-up lying, right side lying or left side lying positions respectively, while displaying as time-varying images the waveforms of cardiograms produced in real time. Therefore, even when proper reference cardiogram production is hindered due to malfunction of electrodes, the cardiograph production may proceed without correcting the problem.

SUMMARY OF THE INVENTION

It is an object of the present invention to provide an electrocardiograph system and its communication device that are capable of measuring and storing the cardiograms for reference corresponding to various postures of the subject based on remote instructions using wireless signals from the outside without having to have a control unit containing switches in the portable cardiograph for selecting the subject's posture from various posture options.

It is another object of the present invention to provide an electrocardiograph system that displays the reference cardiograms as static images, while displaying waveforms of obtained cardiograms in real time as time-varying images or as static images in case of need.

According to an aspect of the present invention, an electrocardiograph system has an electrocardiograph that produces cardiograms and transmits the produced cardiograms, and a communication device that wirelessly communicates with the electrocardiograph. The communication device accepts a subject's posture selected from multiple posture options and transmits a predetermined instruction signal to the electrocardiograph when the posture is accepted. The electrocardiograph stores the cardiogram produced when said instruction signal is received from said communication device, as a reference cardiogram corresponding to the selected posture.

According to another aspect of the present invention, an electrocardiograph system has an input circuit producing cardiograms based on electrical potential changes detected by biological electrodes, an operating unit accepting a subject's posture selected from multiple posture options, a memory storing a cardiogram produced by the input circuit when the operating unit accepts a posture selection as the reference cardiogram corresponding to the selected posture discriminating it from other cardiograms, and a display displaying as a static image the waveform of the reference cardiogram, while sequentially displaying as time-varying images waveforms of cardiograms produced time-sequentially by the input circuit.

According to still another aspect of the present invention, a communication device wirelessly communicating with an electrocardiograph has an operating unit accepting a subject's posture selected from multiple posture options, a transmitting unit transmitting a predetermined instruction signal to the electrocardiograph when the posture is accepted, and a receiving unit receiving a cardiogram produced by the electrocardiograph when the electrocardiograph receives the instruction signal as the reference cardiogram corresponding to the selected posture discriminating it from other cardiograms.

DESCRIPTION OF THE PREFERRED EMBODIMENTS

A preferred embodiment of the present invention will be described below referring to the accompanying drawings.

Figure 1:
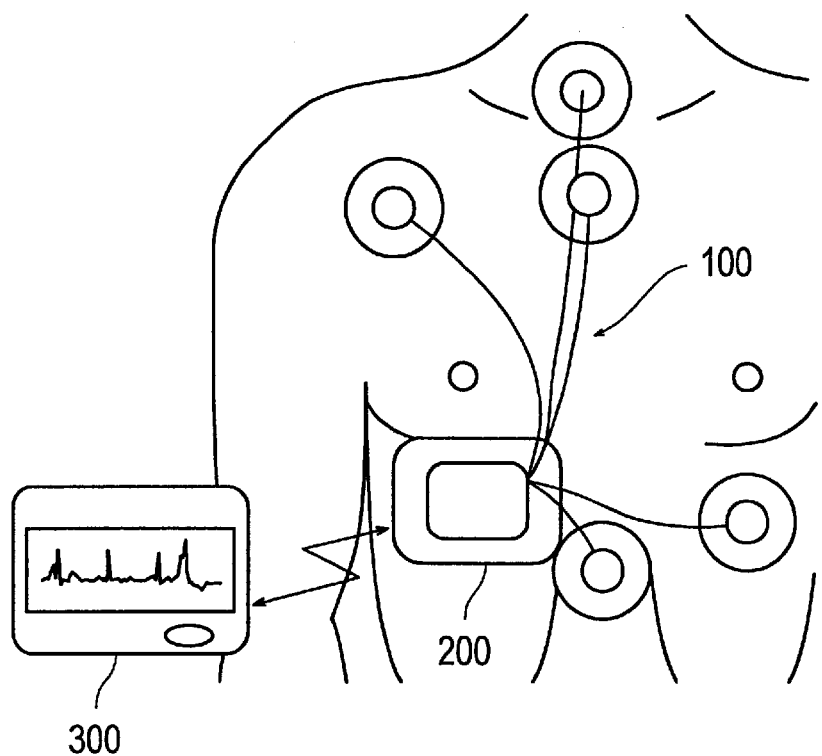
FIG. 1 is an outline drawing of the cardiogram storage device and the monitoring device that constitute the electrocardiograph system.
Figure 2:
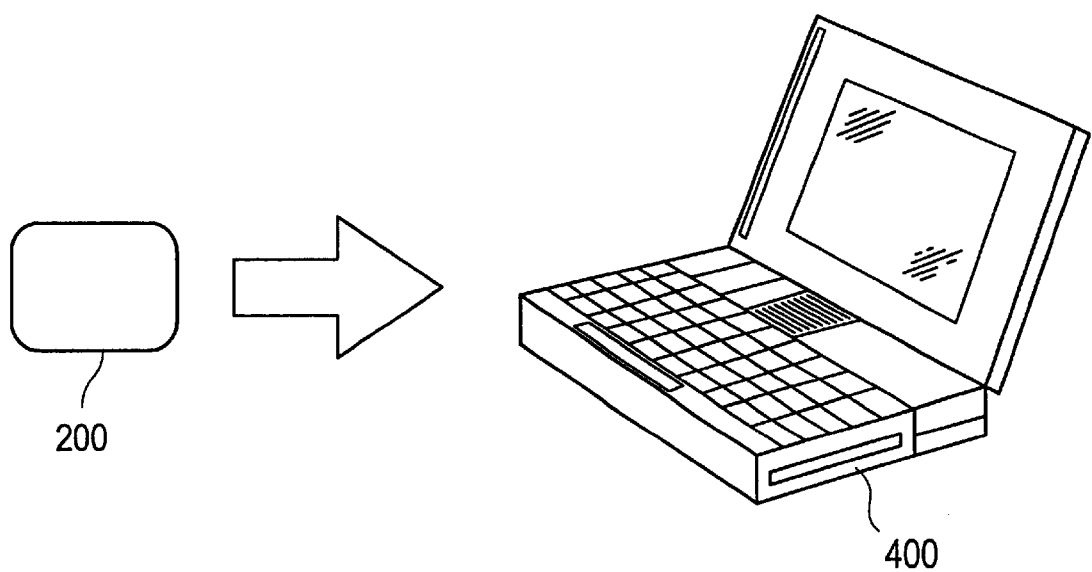
FIG. 2 is an outline drawing of the analyzing device that analyzes cardiograms communicating with the cardiogram storage device shown in FIG. 1.

FIG. 1 shows an electrocardiograph system of a preferred embodiment of the present invention. As shown in FIG. 1, the cardiograph system of the embodiment of the present invention contains a cardiogram storage device (portable electrocardiograph) 200 and a monitoring device (communication device) 300. The cardiogram storage device 200 produces the signals related to cardiograms (hereinafter called simply "cardiograms") based on electrical potential changes detected by biological electrodes 100 adhesively attached to the human body and stores the cardiograms in its memory device. The monitoring device 300 is a communication device that communicates with the cardiogram storage device 200. Furthermore, it is preferable that the electrocardiograph system includes an analyzing device 400 as shown in FIG. 2. The analyzing device 400 analyzes the cardiogram (cardiogram data) produced by the cardiogram storage device 200 as a result of measurement for a period of time (e.g., 24 hours) necessary for diagnosing any disease of the subject. Since the structure of the biological electrodes 100 in the present invention is similar to that of the conventional biological electrodes, its explanation is omitted.

The medical operator selects an appropriate posture from the available options by operating the monitoring device 300 in coordination with the change of the subject's posture. In other words, the monitoring device 300 accepts the posture information for the subject selected from multiple choices of postures. Upon accepting the selection information, the monitoring device 300 instructs the cardiogram storage device 200 to store the reference cardiogram corresponding to the selected posture. Specifically, the monitoring device 300 wirelessly transmits a signal instructing to store the reference cardiogram to the cardiogram storage device 200 (hereinafter "reference cardiogram storage instruction").

The cardiogram storage device 200 obtains each cardiogram sequentially through measurement for a predetermined time period and stores the obtained cardiograms. When the cardiogram storage device 200 receives the reference cardiogram storage instruction wirelessly from the monitoring device 300, the cardiogram storage device 200 stores the cardiogram obtained by a measurement when the instruction was received as the reference cardiogram for the corresponding posture discriminating it from other cardiograms.

When the measurement for a necessary cardiogram for a period of time and its storage are completed, a communication is executed between the cardiogram storage device 200 and the analyzing device 400 (FIG. 2). The analyzing device 400 compares the cardiogram to be analyzed, which is the result of measurement conducted for the predetermined time period by the cardiogram storage device 200, with the reference cardiograms. The analyzing device 400 differentiate the change of the cardiogram due to the subject's disease and the change due to the change in the posture of the subject. Consequently, the analyzing device 400 is capable of executing a cardiogram analysis with a high accuracy.

Figure 3:
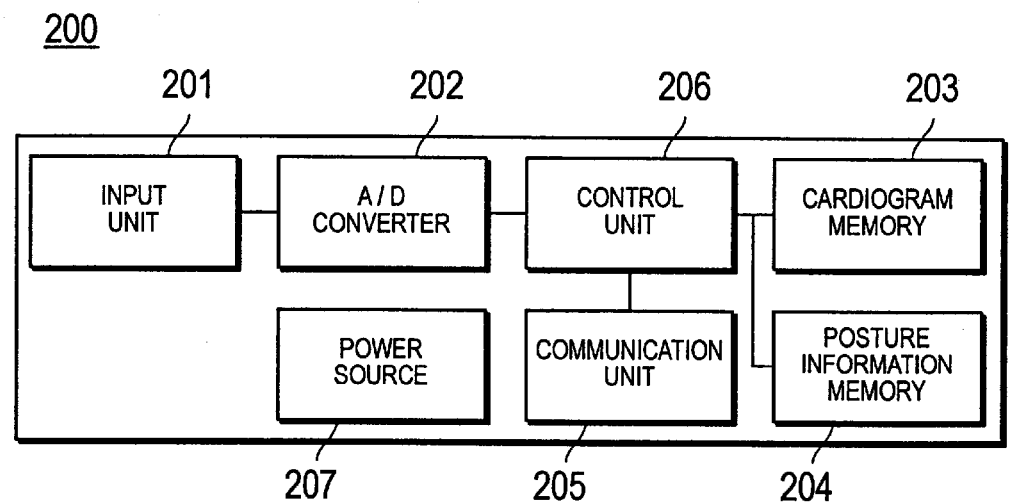
FIG. 3 is a block diagram that shows the constitution of the cardiogram storage device shown in FIG. 1.

FIG. 3 is a block diagram that shows the constitution of the cardiogram storage device.

An input unit 201 is an input circuit for measuring cardiograms based on electrical potential changes detected by the biological electrodes 100. An A/D converter 202 digitalizes the cardiogram obtained by the input unit 201. A cardiogram memory 203 stores the cardiogram produced by measuring for the predetermined period and digitalized. The posture information memory 204 establishes and stores a piece of information (pointer) for specifying a portion that corresponds to the reference cardiogram from a series of cardiograms stored in the cardiogram memory 203, and stores it. For example, this pointer is an address on the cardiogram memory 203 where the cardiogram that was produced when the cardiogram storage device 200 received the reference cardiogram storage instruction is stored. Due to the use of the constitution of storing the pointer, it is possible to store the reference cardiogram discriminating it from other cardiograms. With this constitution, it is also possible to save the memory resources in comparison to the case of extracting the area corresponding to the reference cardiogram from the entire pack of produced cardiograms and storing the data of the extracted reference cardiogram into a separate memory area.

A storage device side communication unit 205 is an interface for wirelessly communicating with the monitoring device 300 and/or the analyzing device 400. More specifically, the storage device side communication unit 205 communicates with the monitoring device 300 through electromagnetic coupling. The storage device side communication unit 205 functions as a receiving unit that receives control signals and reference cardiogram storage instructions from the monitoring device 300, and a transmitting unit for wirelessly transmitting cardiograms and pointers stored in the cardiogram memory 203. A control unit 206 is a CPU that controls the cardiogram storage device 200 entirely. A power source 207 supplies power to various units.

Figure 4:
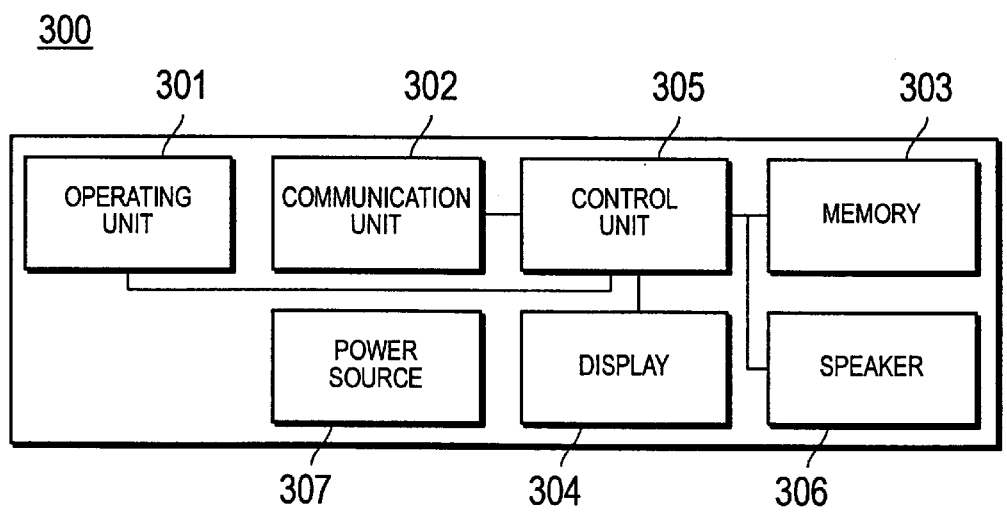
FIG. 4 is a block diagram showing the constitution of the monitoring device shown in FIG. 1.

FIG. 4 is a block diagram showing the constitution of the monitoring device in the present embodiment. An operating unit 301 consists of switches and/or pushbuttons that are operated by the user such as a medical operator as described later. The operating unit 301 is used for selecting the posture of the subject. It is one of the features of the present invention that the operating unit 301 is not provided in the cardiogram storage device (portable electrocardiograph) 200 itself, but rather in the monitoring device 300 (communication device) that wirelessly communicates with the cardiogram memory device (electrocardiograph) 200. Consequently, it is possible to produce and store the reference cardiogram corresponding to each posture based on a remote instruction received from the outside wirelessly without having to have a control unit containing switches, etc., in the portable cardiograph itself for receiving the posture selection selected from various posture options for the subject.

A monitor side communication unit 302 is an interface for wirelessly communicating with the cardiogram storage device 200. The monitor side communication unit 302 wirelessly transmits the reference cardiogram storage instruction to the cardiogram storage device 200 when the operating unit 301 accepts the posture selection. The monitor side communication unit 302 further has the capability of receiving the cardiogram produced by the cardiogram storage device 200 in real time as well as the capability of receiving the reference cardiogram itself or the aforementioned pointer for specifying the reference cardiogram. A memory 303 temporarily stores cardiograms and various data received by the monitor side communication unit 302.

A display 304 is typically a small liquid crystal panel. The display 304 displays the waveforms of cardiograms received time-sequentially from the cardiogram storage device 200 in time-varying images. Moreover, it displays the waveforms of reference cardiograms (posture waveforms) received from the cardiogram memory device 200 as static images for the predetermined time period. This is another feature of the present invention. Consequently, the present invention enables to display not only the waveforms of produced cardiograms as time-varying images but also the waveforms of the reference cardiograms corresponding to various postures such as standing, face-up lying, right side lying and left side lying positions as static images. Since the waveforms of the reference cardiograms are displayed as static images, the user can visually and securely inspect whether the reference cardiograms are accurately produced.

A control unit 305 is a CPU that controls the monitoring device entirely. For example, the control unit 305 controls the contents that are displayed on the display 304.

A speaker 306 outputs various alarm sounds. For example, the speaker 306 functions as a notifying means for notifying the completion of the process for the reference cardiograms to the user. A power source 307 supplies power to various units. As a deviation from this embodiment, the speaker 306 can be omitted.

Figure 5:
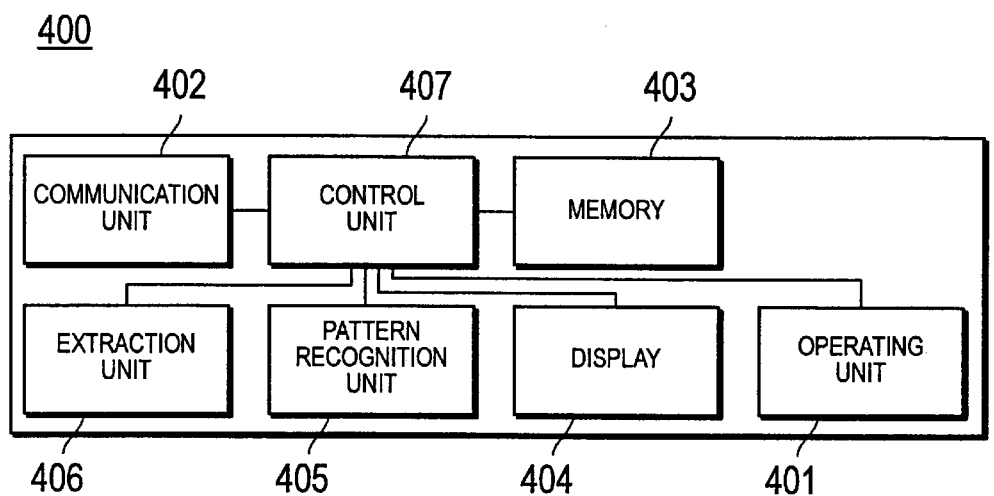
FIG. 5 is a block diagram showing the constitution of the analyzing device shown in FIG. 2.

FIG. 5 is a block diagram that shows the constitution of the analyzing device in this embodiment. The analyzing device 400 is capable for classifying the measurement results of the stored cardiograms into normal heartbeats and abnormal heartbeats and counting the numbers of those heartbeats.

An operating unit 401 consists of a keyboard and/or a pointing device such as a mouse. An analyzer side communication unit 402 is an interface for communicating with the cardiogram storage device 200. The analyzer side communication unit 402 wirelessly receives cardiograms to be analyzed that are produced by the cardiogram storage device 200 for the predetermined time period from the cardiogram storage device 200. It also receives the one or more pointers stored in the posture information memory 204 from the cardiogram storage device 200. The analyzing device 400 acquires the reference cardiograms corresponding to various postures based on the pointers. The memory 403 stores various data received via the analyzer side communication unit 402. The display 404 displays the contents of the instructions, process execution conditions, and analysis results received from the operating unit 401.

A pattern recognition unit 405 performs the pattern recognition of the waveforms of the reference cardiograms. An extraction unit 406 compares the cardiogram data produced by the cardiogram storage device 200 for the predetermined time period with the reference cardiograms based on the pattern recognition results. The extraction unit 406 extracts the changes of the cardiograms due to a posture change based on the comparison results. The extraction unit 406 further discriminates whether the cardiogram changes are due to the posture changes or other causes (such as disease).

A control unit 407 is a CPU that controls the analyzing unit 400 and executes arithmetic operations. The above mentioned pattern recognition unit 405 and the extraction unit 406 may typically realized by computer programs installed on a hard disk (not shown). A control unit 407 executes the program.

Figure 6:
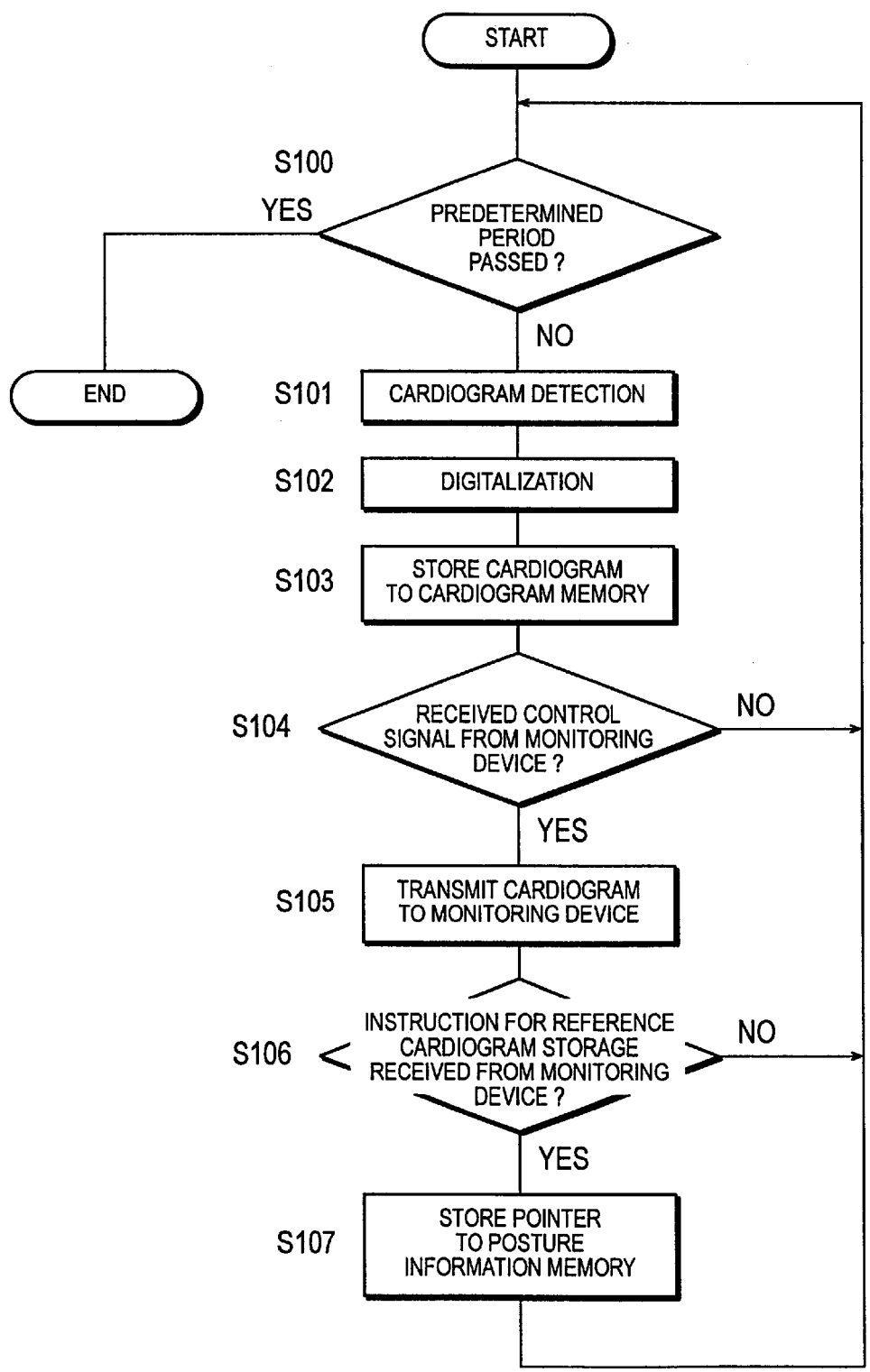
FIG. 6 is a flowchart showing the process of the cardiogram storage device shown in FIG. 3.

FIG. 6 is a flowchart showing the process contents of the cardiogram storage device. The input unit 201 measures to produce cardiograms based on electrical potential changes detected by the biological electrodes 100 (step S101). The biological electrodes 100 include ECG (electrocardiography) sensor electrodes and reference electrodes. The input unit 201 differentially amplifies the potentials detected by the ECG sensor electrodes and deletes the external noises by means of the potentials provided by the one or more reference electrodes. Produced cardiograms are analog signals. The A/D converter 202 converts these cardiograms into digital signals by means of A/D conversion (step S102). Cardiograms converted into digital signals are stored into predetermined memory regions of the cardiogram memory 203 in real time (step S103).

Next, a judgment is made whether any control signals (command signals) are received from the monitoring device 300 (step S104). As described later, the monitoring device 300 transmits control signals to the outside via the monitor side communication unit 302. When the user such as a medical operator brings the monitor side communication unit 302 and the storage device side communication unit 205 within the communication distance wherein they can be magnetically coupled, the storage device side communication unit 205 receives control signals from the monitor side communication unit 302. The communication distance is typically 1 cm through 100 cm, more preferably 1 cm through 10 cm. When a control signal is received (step S104: Yes), the process of the step S105 is executed. In the step S105, the cardiograms produced at the step S103 are stored into the cardiogram memory 203 and are transmitted essentially simultaneously from the storage device side communication unit 205 to the monitor side communication unit 302 in time-sequentially.

Further, a judgment is made whether any reference cardiogram storage instruction is received from the monitoring device 200 (step S106). If the storage device side communication 205 receives a reference cardiogram storage instruction (step S106: Yes), the pointer is stored into the posture information memory 204 (step S107). The cardiogram storage device 200 thus stores the cardiograms produced by measuring for the predetermined time period into the cardiogram memory 203 and a pointer for specifying a portion of a series of cardiograms stored in the cardiogram memory 203 that corresponds to the reference cardiogram.

Consequently, it is possible to store the cardiogram produced when the reference cardiogram storage instruction was received from the monitoring device 300 as the reference cardiogram corresponding to the selected posture discriminating it from other reference cardiograms. In step S100, the process of the cardiogram storage device is finished when the cardiogram storage device produces the cardiogram by measuring for predetermined period of time (e.g., 24 hours).

Figure 7:
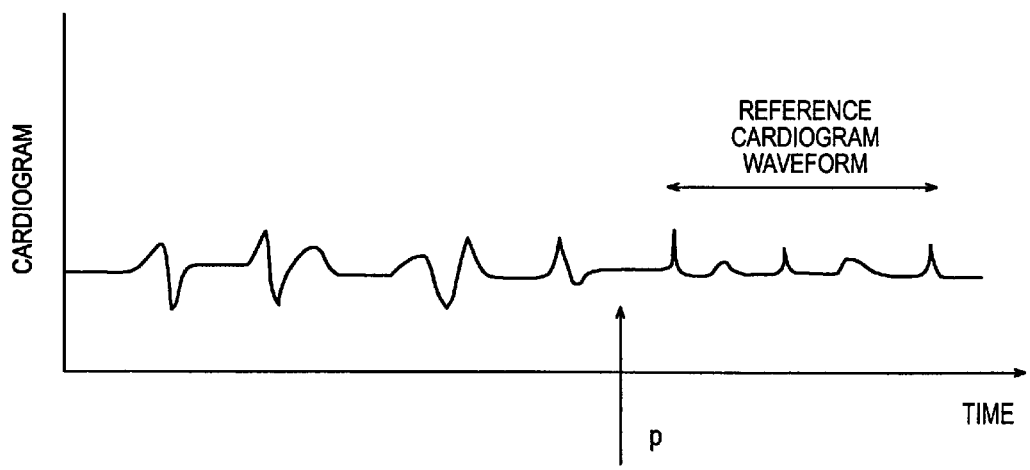
FIG. 7 is a chart conceptually showing an example waveform when the posture of the subject changes.

FIG. 7 is a typical cardiogram wherein the posture of the subject changes. The posture of the subject changes at the point P in the chart. As mentioned before, the monitoring device 300 normally transmits a reference cardiogram storage instruction when the operating unit 301 of the monitoring device 300 is operated in accordance with the change of the subject's posture. Therefore, the cardiogram storage device 200 receives the reference cardiogram instruction at the point P in the chart. Consequently, the cardiogram produced when the reference cardiogram storage instruction is received will be stored as the cardiogram at the time of the posture change, i.e., the reference cardiogram. More preferably, the address on the cardiogram memory 203 where the cardiogram produced at the time of the point P is stored in the posture information memory 204 as the pointer.

Incidentally, the reference cardiogram storage instruction may include the information related to the selected posture. In such a case, it is preferable to store the reference cardiogram and the type of posture. Consequently, it is possible to produce and store reference cardiograms in correspondence with each posture such as the standing, face-up lying, right side lying and left side lying positions.

Figure 8:
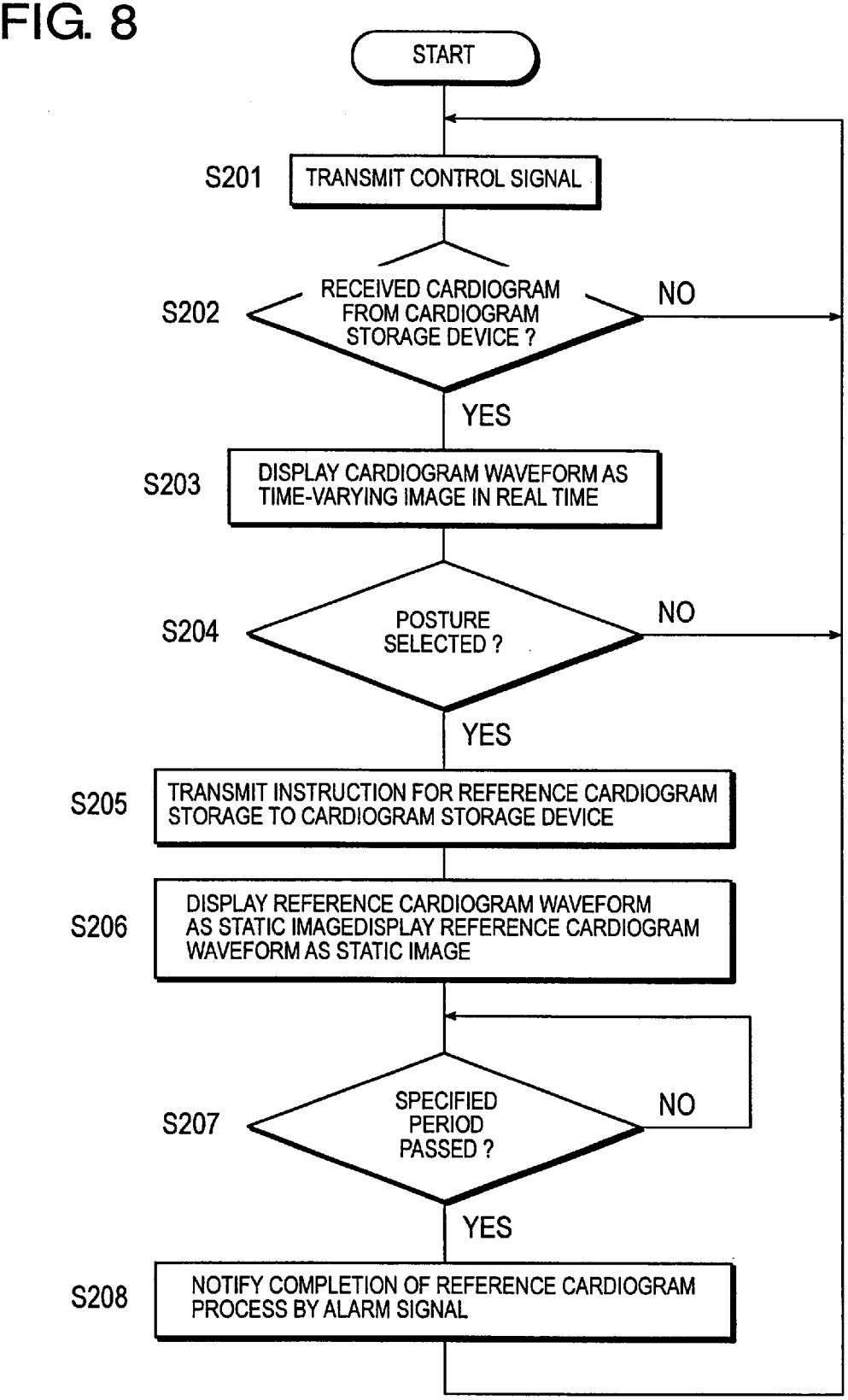
FIG. 8 is a flowchart showing the process of the monitoring device shown in FIG. 4.

FIG. 8 is a flowchart showing the process contents of the monitoring device. The monitoring device 300 constantly transmits control signals under the operating condition (step S201). When a cardiogram is received from the cardiogram storage device 200 (step S202: Yes), the control unit 305 displays time-serially the waveforms of the received cardiogram received from the cardiogram storage device 200 (S203). The display of the waveforms of cardiograms by the monitoring device 300 is used for making a judgment whether the connection condition between the cardiogram storage device 200 and the biological electrodes 100 is good. The monitoring device 300 should display the waveforms of cardiograms only when the operating condition of the cardiogram storage device 200 is to be checked. Thus, it is not necessary for the monitoring device 300 to display cardiograms during the process of measuring cardiograms necessary for diagnosing the subject's illness.

In the step S204, a judgment is made whether the operating unit 301 received the posture selection for the subject. If it has received the posture selection (step S204: Yes), the process of the step S205 is executed.

Figure 9:
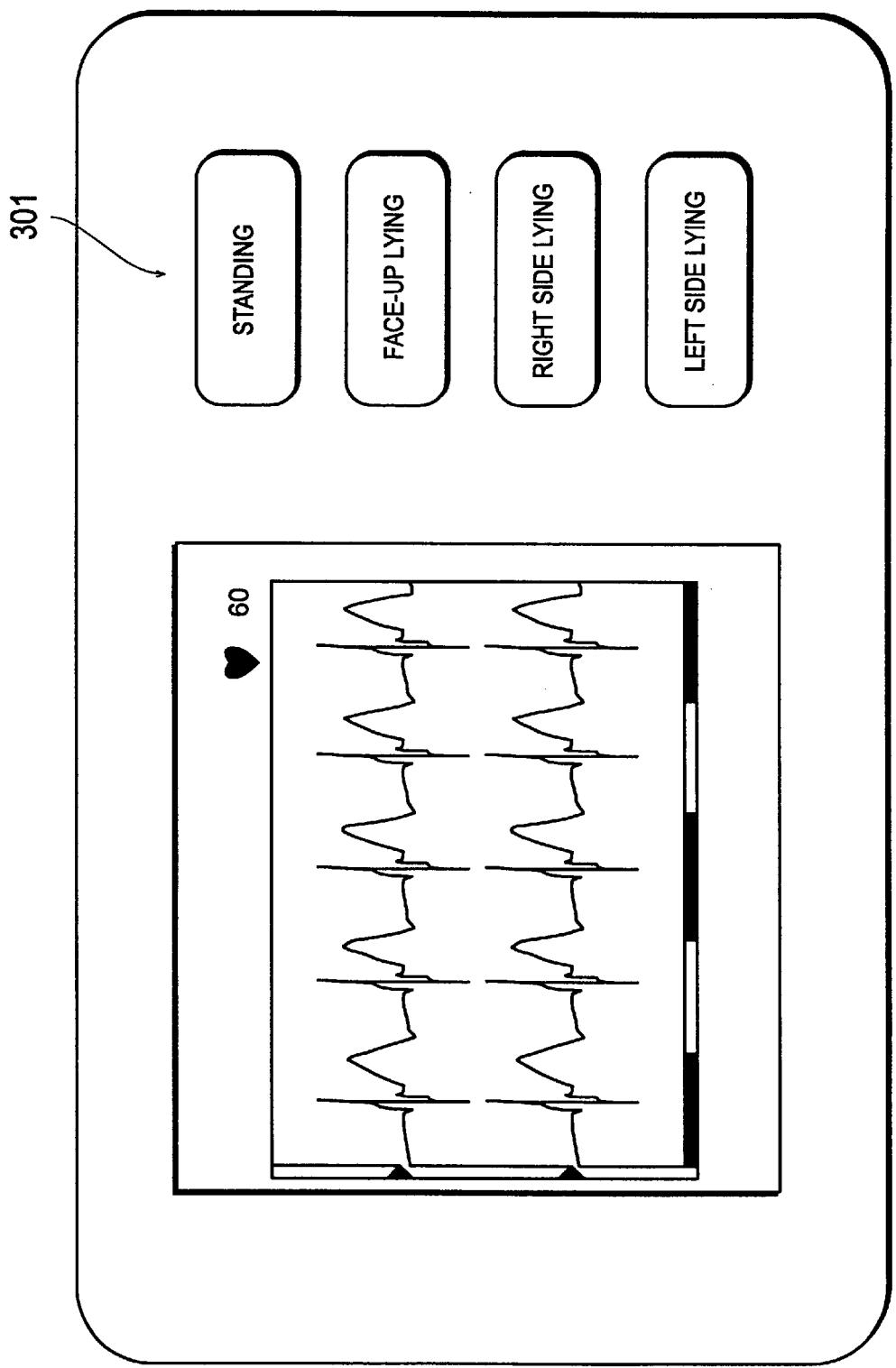
FIG. 9 is an example of the operating unit provided in the monitoring device shown in FIG. 4.

FIG. 9 shows an example of the operating unit provided in the monitoring device. In the case shown in FIG. 9, the operating unit 301 is provided with posture selection switches name-tagged for the standing, face-up lying, right side lying and left side lying positions. If the subject's posture changed to the face-up lying position, the user such as a medical operator selects the switch for the face-up lying position from the bank of posture selection switches and operates it. As a result, the face-up lying position is selected and accepted.

Figure 10:
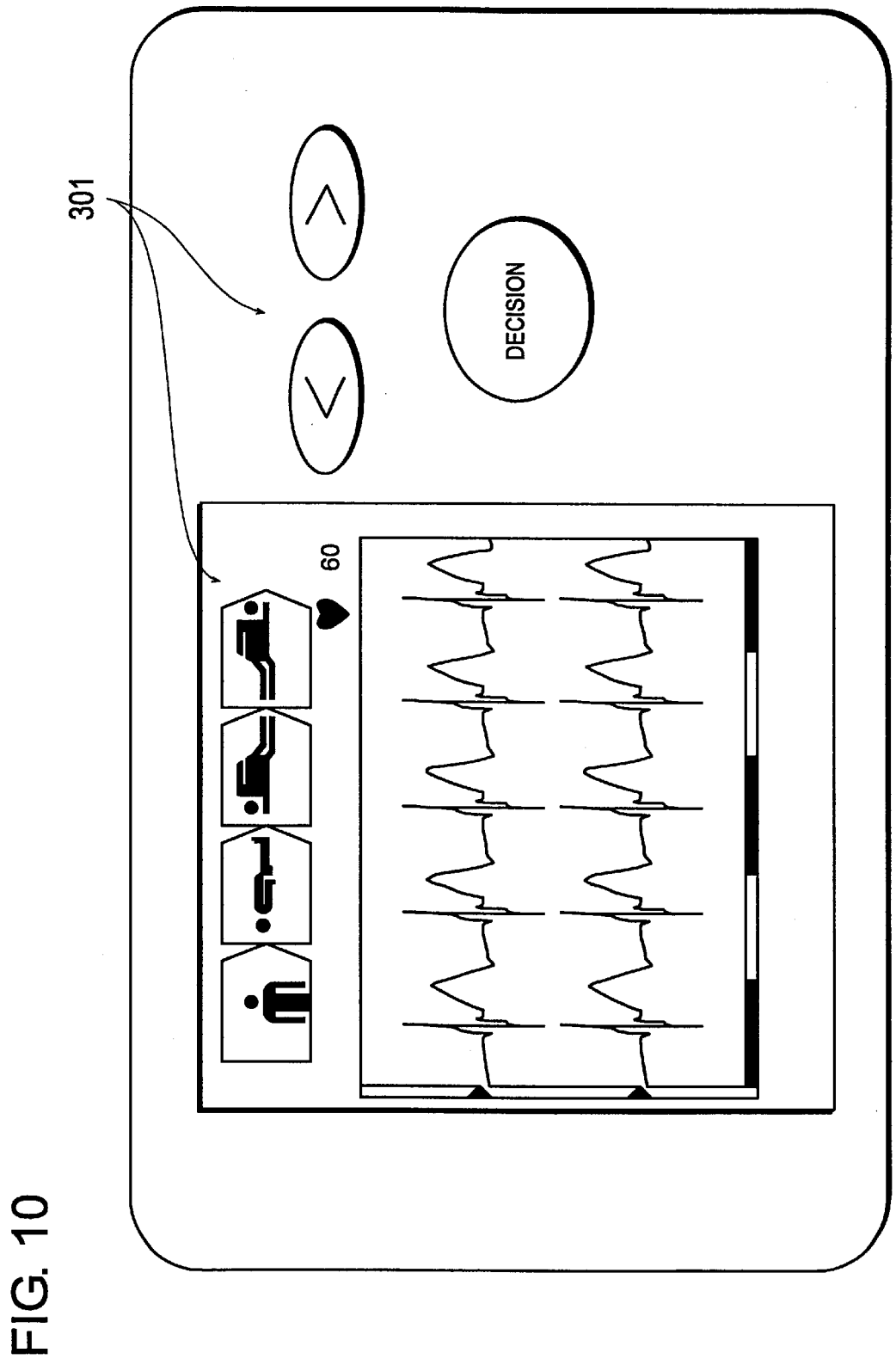
FIG. 10 is a drawing showing another example of the operating unit provided in the monitoring device shown in FIG. 4.

FIG. 10 is another example of the operating unit. In the case shown in FIG. 10, the operating unit 301 is equipped with a posture display unit that displays a mark that corresponds to a selected posture, selection buttons for freely changing the display of the posture display unit, and the decision button for finally approving the posture selection. Thus, the operating unit 301 shown in FIG. 9 or FIG. 10 can accepts the desired selection of the subject's posture.

In the step S205 shown in FIG. 8, the monitor side communication unit 302 wirelessly transmits the reference cardiogram storage instruction to the cardiogram storage device 200 when the posture selection is accepted.

The control unit 305 receives the reference cardiogram, transmitted from the cardiogram storage device 200 in response to the reference cardiogram storage instruction. The display 304 displays the waveforms of the reference cardiograms received from the cardiogram storage device 200 as static images (step S206). Thus, the display 304 displays essentially the reference cardiograms as static image, while displaying as time-varying image waveforms of the cardiograms received in real time from the cardiogram storage device 200. Consequently, the user such as a medical operator can easily confirm the reference cardiograms as static images. Further, if the user determines that that reference cardiograms cannot be produced properly due to improper installations of the biological electrodes, etc., as a result of the confirmation of the waveforms of the reference cardiograms displayed as static images, the user can correct the installations of the biological electrodes so that proper reference cardiograms can be produced.

After waiting for a predetermined time period passes (step S207: Yes), the speaker 306 notifies by an alarm sound the user that the process concerning the reference cardiograms has been completed (step S208). This specific time period is typically several to several tens of seconds. In place of the issuing of the alarm sound by the speaker 306, the completion of the process concerning the reference cardiograms can be notified by means of a display on the display unit 304.

The storage of the reference cardiograms corresponding to various postures is completed by means of the procedures described above referring to FIG. 6 and FIG. 8. Each reference cardiogram is stored so that it can be read out by a specific pointer. After that, the cardiogram storage device 200 produces a cardiogram for a specific measuring time required for diagnosis of a particular disease similar to a case of a conventional electrocardiograph system, and stores the produced cardiogram.

Figure 11:
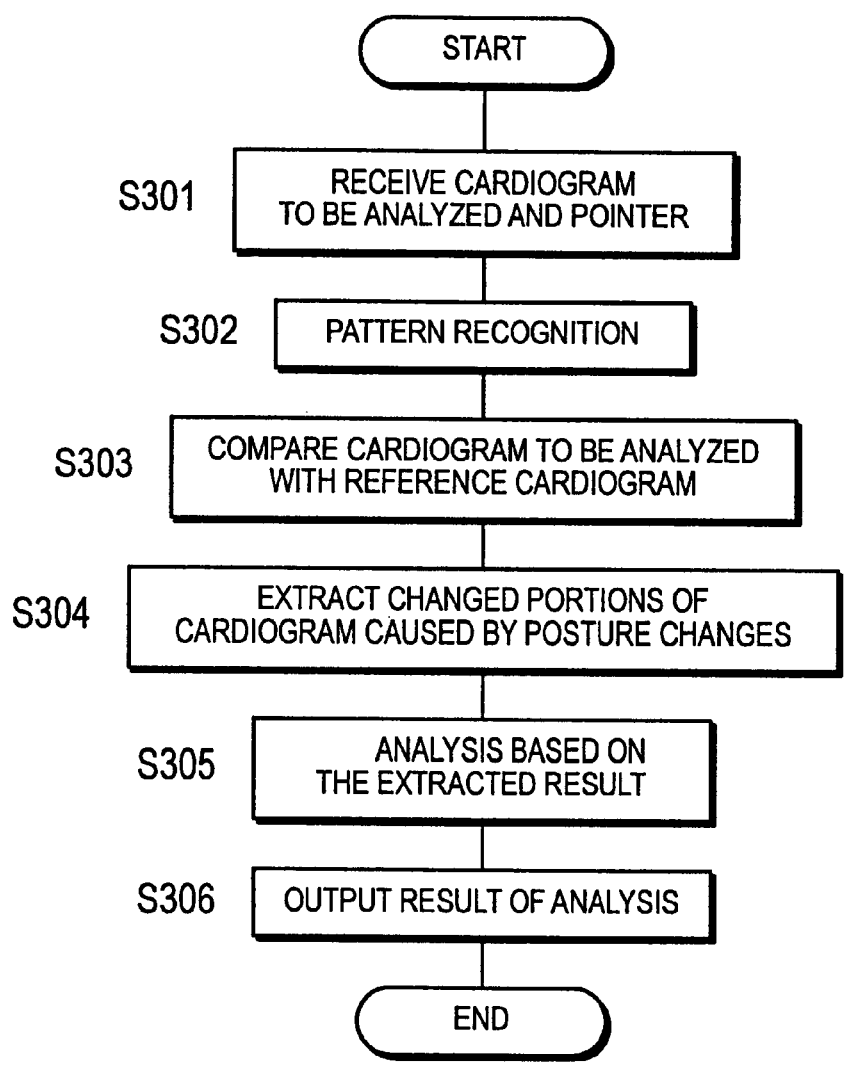
FIG. 11 is a flow chart showing the process of the analyzing device shown in FIG. 5.

Next, the procedure for the analysis of the cardiogram data will be described. FIG. 11 is a flowchart showing the process contents of the analyzing device 400.

First, the analyzer side communication unit 402 communicates with the cardiogram storage device 200 that has produced a cardiogram by measuring for the predetermined time period. Consequently, the analyzer side communication unit 402 wirelessly receives the cardiogram produced by measuring for the predetermined time period from the cardiogram storage memory device 200. Further, the analyzer side communication unit 402 receives the pointer stored in the posture information memory 204 (step S301).

Based on the received pointers, a reference cardiogram is acquired for each posture. Further, the wave patterns of the acquired reference cardiograms are recognized (step S302). The cardiograms produced by measuring for the predetermined period of time are compared with the reference cardiograms (step S303). As a result, the changes of the cardiograms due to disease are discriminated from the changes due to posture changes. The recognition of waveform patterns can be conducted by using the conventional pattern recognition method.

The portions where the cardiograms changed due to posture changes are extracted from the cardiogram data measured for a period necessary for diagnosis (step S304). After that, an analysis is made here whether there are any heartbeat areas in the cardiograms including extracted portions. The number of the abnormal heartbeat portions is counted (step S305). The result of the analysis is outputted on paper by a printer (not shown), or outputted on the display 405 (step S306).

According to the process shown in FIG. 11, the accuracy of the analysis can be substantially improved as the analysis of the cardiograms is done using the reference cardiograms actually produced for each subject. Specifically, even if there are large discrepancies between reference cardiograms due to personal differences between the subjects, it is possible to discriminate the changes in the cardiograms due to posture changes and the changes in the cardiograms due to disease such as ischemic heart disease, facilitating the final judgment of the medical operator.

Moreover, it is possible to conduct the analysis using reference cardiograms corresponding to various postures with not just the standing and side lying positions but also face-up lying, the left side lying, and right side positions, so that an analysis with a higher accuracy is possible.

While the above description was about a preferable embodiment of the present invention, it goes without saying that various changes, additions and simplifications are possible within the scope of this invention described in the claims.

For example, while the above description dealt with an application of the present invention to an electrocardiograph system of a type wherein the monitoring device is separated from the cardiogram storage device that is directly attached to the body of the subject, the present invention includes an electrocardiography system wherein the cardiogram storage device and the monitoring device are formed integrally system displaying the waveforms of the cardiograms produced time-sequentially as time-varying images sequentially and displaying also, when the subject's posture is selected, the waveforms of the reference cardiograms as static images.

Further, while the case of using electromagnetic coupling as means of communications between the cardiogram storage device, the monitoring device and the analyzing device, other wireless means such as infrared communications can be used as well. Although it is preferable to form a small monitoring device and a relatively large analyzing device as separate units from the standpoint of making handling easier, the monitoring device and the analyzing device can be formed as an integral device as well.

Furthermore, it is also possible not only to use the result of comparison between the cardiogram produced by measuring for the predetermined time period, which is the object of analysis, and the reference cardiograms, but also to separate and extract precisely the portion where a change occurred due to a posture change by means of the duration period of the change occurred on the cardiogram and/or its cycle.

In the above description, the cardiogram memory for storing the cardiograms that are produced time-sequentially by the cardiogram storage device is provided separate from the posture information memory where the pointers for identifying a particular reference posture waveform. However, the present invention is not limited to such a constitution, and it can be applied to a case where the cardiograms and the pointers are stored in the same memory device.

Moreover, it was described in the above that the reference cardiograms are discriminated from other cardiograms by means of the stored pointers. However, the present invention is not limited by such a constitution, but rather it can have a constitution wherein the diagram produced by measuring is extracted and stored separately at the point when the reference cardiogram storage instruction is received.

This application is based on Japanese Patent Application No. 2000-379251 filed on Dec. 13, 2000, the contents of which are hereby incorporated by reference.

What is claimed is:

1. Electrocardiograph system comprising:
   an electrocardiograph producing cardiograms, and transmitting the produced cardiograms;
   a communication device wirelessly communicating with said electrocardiograph; wherein,
      said communication device accepts a subject's posture selected from multiple posture options and transmits a predetermined instruction signal to said electrocardiograph when the posture is accepted; and
      said electrocardiograph stores the cardiogram produced when said instruction signal is received from said communication device as a reference cardiogram corresponding to the selected posture.

2. Electrocardiograph system of claim 1, wherein
   said electrocardiograph transmits the produced cardiogram to said communication device;
   said communication device has a display unit, which displays as a static image the waveform of said reference cardiogram received from said electrocardiograph in response to said instruction signal, while sequentially displaying as time-varying images waveforms of cardiograms received time-sequentially from said electrocardiograph.

3. Electrocardiograph system of claim 1, wherein
   said instruction signal transmitted from said communication device includes information about the selected posture.

4. Electrocardiograph system of claim 1, wherein
   said communication device is a portable terminal device.

5. Electrocardiograph system of claim 1, wherein
   said communication device communicates with said electrocardiograph by electro-magnetic coupling.

6. Electrocardiograph system of claim 1, wherein
   said communication device communicates with said electrocardiograph by infrared rays.

7. Electrocardiograph system of claim 1, wherein
   said multiple posture options include a standing position and a face-up lying position.

8. Electrocardiograph system of claim 1, wherein
   said multiple posture options include a standing position, a face-up lying position, a right side lying position, and a left side lying position.

9. Electrocardiograph system of claim 8, wherein
   said communication device has an operating unit provided with multiple marks corresponding respectively to said standing, face-up lying, right side lying, and left side lying positions, by means of which the selection of each posture is entered.

10. Electrocardiograph system of claim 1, wherein
    said electrocardiograph stores cardiograms produced for a predetermined period and stores also information for identifying portions that correspond to said reference cardiogram from a series of cardiograms thus stored.

11. Electrocardiograph system of claim 1 further comprising an analyzing device that analyzes cardiograms; wherein said analyzing device wirelessly receives from said electrocardiograph said reference cardiogram and the cardiograms produced by said electrocardiograph for the predetermined period, and compares the cardiograms produced by said electrocardiograph for the predetermined period with said reference cardiogram.

12. Electrocardiograph system of claim 11, wherein said analyzing device discriminates changes in the cardiograms caused by disease from changes caused in the cardiograms caused by posture changes of the subject based on the result of comparing, and counts the number of abnormal heartbeats contained in the cardiograms.

13. Electrocardiograph system comprising:

an input circuit producing cardiograms based on electrical potential changes detected by biological electrodes;

an operating unit accepting a subject's posture selected from multiple posture options;

a memory storing a cardiogram produced by said input circuit when said operating unit accepts a posture selection as the reference cardiogram corresponding to the selected posture discriminating it from other cardiograms; and a display displaying as a static image the waveform of said reference cardiogram, while sequentially displaying as time-varying images waveforms of cardiograms produced time-sequentially by said input circuit.

14. Communication device wirelessly communicating with an electrocardiograph comprising:

an operating unit accepting a subject's posture selected from multiple posture options;

a transmitting unit transmitting a predetermined instruction signal to said electrocardiograph when the posture is accepted; and a receiving unit receiving a cardiogram produced by the electrocardiograph when the electrocardiograph receives said instruction signal as the reference cardiogram corresponding to the selected posture discriminating it from other cardiograms.

15. Electrocardiograph system of claim 13, wherein said display displays the waveform of said reference cardiogram as a static image at a time when said reference cardiogram is stored in said memory.

16. Electrocardiograph system of claim 13, wherein the input circuit forms a part of a first device and the operating unit forms a part of a second device, the first and second devices being separate from one another and communicating with one another wirelessly.

17. Electrocardiograph system of claim 13, wherein the input circuit forms a part of a storage device, and the operating unit forms a part of a monitoring device that also includes a communication unit which transmits a reference cardiogram storage instruction to the storage device when the operating unit accepts the posture selection as the reference cardiogram.

18. Electrocardiograph system of claim 13, wherein the monitoring device receives the reference cardiogram from the storage device in response to the reference cardiogram storage instruction received by the storage device, with the display displaying the static image of the waveform of the reference cardiogram.

19. Electrocardiograph system of claim 13, wherein the operating unit and the display are provided together on a single unit.

20. Electrocardiograph system of claim 13, wherein said single unit is a monitoring device.

* * * * *